United States Patent

Krumme

(10) Patent No.: US 9,112,366 B2
(45) Date of Patent: Aug. 18, 2015

(54) CONTACTLESS ROTARY JOINT WITH SAFETY FUNCTION

(75) Inventor: Nils Krumme, Feldafing (DE)

(73) Assignee: Schleifring Und Apparatebau GmbH (DE)

( * ) Notice: Subject to any disclaimer, the term of this patent is extended or adjusted under 35 U.S.C. 154(b) by 353 days.

(21) Appl. No.: 13/482,165

(22) Filed: May 29, 2012

(65) Prior Publication Data

US 2012/0307977 A1    Dec. 6, 2012

(30) Foreign Application Priority Data

May 30, 2011   (EP) ..................................... 11168041
Jul. 1, 2011   (EP) ..................................... 11172372

(51) Int. Cl.
  *H02J 5/00*   (2006.01)
  *A61B 6/00*   (2006.01)
  *A61B 6/03*   (2006.01)
  *A61B 6/10*   (2006.01)

(52) U.S. Cl.
  CPC ................ *H02J 5/005* (2013.01); *A61B 6/032* (2013.01); *A61B 6/10* (2013.01); *A61B 6/56* (2013.01)

(58) Field of Classification Search
  CPC ............ A61B 6/56; A61B 6/032; H05G 1/10; H05G 1/12; H05G 1/14; H05G 1/18; H02J 5/005; H01F 38/18
  USPC ......................................................... 378/15
  See application file for complete search history.

(56) References Cited

U.S. PATENT DOCUMENTS

| | | | |
|---|---|---|---|
| 4,200,795 A | 4/1980 | Kawamura et al. | |
| 4,797,908 A | 1/1989 | Tanaka et al. | |
| 5,737,197 A | 4/1998 | Krichtafovitch et al. | |
| 7,054,411 B2 | 5/2006 | Katcha et al. | |
| 2009/0276199 A1* | 11/2009 | Krumme et al. | 703/7 |
| 2010/0090536 A1* | 4/2010 | Krumme et al. | 307/104 |
| 2011/0075796 A1* | 3/2011 | Loef et al. | 378/15 |

FOREIGN PATENT DOCUMENTS

| | | |
|---|---|---|
| CN | 102810913 A | 12/2012 |
| EP | 2530805 A1 | 12/2012 |
| WO | 2008079870 A2 | 7/2008 |

\* cited by examiner

*Primary Examiner* — Glen Kao
(74) *Attorney, Agent, or Firm* — Yakov Sidorin; Quarles & Brady LLP

(57) ABSTRACT

Inductive rotary joint system with stationary and rotating sides has a one-phase rectifier for receiving one-phase AC-input to generate low-level DC-voltage, and a three-phase rectifier for receiving three-phase input to generate higher-level DC-voltage. An AC-power generator receives DC-voltage and generates AC-power, which is coupled by an inductive rotary joint to a load at the rotating side. Voltage coupled to the load is comparably higher when the one-phase rectifier is connected and comparably lower when the three-phase rectified is connected. A control unit at the secondary side for controlling at least the load is connected to measure the voltage produced for the secondary side, and to distinguish between a comparatively lower voltage and a comparatively higher voltage. When a presence of a comparatively higher voltage is indicated, an x-ray tube is enabled within the load.

15 Claims, 1 Drawing Sheet

CONTACTLESS ROTARY JOINT WITH SAFETY FUNCTION

PRIORITY CLAIM

This application claims priority to pending European Application No. 11172372.2 filed on 1 Jul. 2011 and abandoned European Application No. 11168041.9 filed on 30 May 2011.

BACKGROUND OF THE INVENTION

1. Field of the Invention

The invention relates to an inductive power coupling device for coupling electrical power between two units being rotatable against each other, specifically for power couplers used in computer tomography scanners. Such power couplers are also known as rotary joints.

2. Description of Relevant Art

In computer tomography scanners and other related machines high-power in the range of 10 kW up to more than 100 kW is transferred from the stationary the rotating side. There a high voltage in the range of above hundred kilovolts is generated to produce x-ray radiation. The high voltage and the x-ray radiation may cause physical damage to operating personal under specific conditions like during service when protective covers are open. Furthermore unwanted exposure to x-ray radiation may occur in the case of fault of components responsible for control of the x-ray tube.

In the U.S. Pat. No. 7,054,411 a multiple channel inductive rotary joint is disclosed. It has a first inductive channel for transferring auxiliary power from the stationary to the rotating side. This auxiliary power is required by the control circuits on the rotating side to operate correctly. There is a separated high power inductive channel for transferring x-ray power from primary to secondary side. Furthermore a capacitive feedback link for power control is provided. The disadvantage of this system is the very high complexity, high costs for multiple channels and the high rotating mass due to two inductive rotary joints requiring heavy ferrite cores.

SUMMARY OF THE INVENTION

The embodiments are based on the object of providing a simple, cost efficient rotary joint which still provides a simple and reliable signaling to switch a load on the rotating side from the stationary side. High security and protection of the operating personal shall be achieved.

A further aspect of the invention is to provide a system which is tolerant against a first failure case.

In an embodiment, on the stationary side an inductive rotary joint system has a first input circuit which may be a one phase rectifier for receiving a one phase AC input, generating a comparatively lower DC voltage. For the case of 230V line voltage, the output voltage of the one phase rectifier is approximately 230V*sqrt(2)=325V. Furthermore a second input circuit which may be a three phase rectifier is provided for receiving a three phase input, generating a comparatively higher DC voltage. For the case of 400V line voltage in three phase operation, the output voltage of the three phase rectifier is approximately 400V*sqrt(2)=565V. To distinguish reliably between a comparatively lower voltage and a comparatively higher voltage, the ratio between the comparatively higher voltage and the comparatively lower voltage should be greater than 1.1 which means that the comparatively higher voltage is at least 1.1 times the comparatively lower voltage. Preferably this ratio is higher than 1.5 and most preferably higher than 2. The input circuits are coupled to deliver power to the AC power generator. Preferably their outputs are connected in parallel. Optionally a switch may be provided to connect at least one of the input circuits to the AC power generator. The DC voltage from the input circuits or rectifiers is preferably filtered by a filtering circuit (23). An AC power generator generates an AC signal from the DC voltage, typically in the frequency range of 25 kHz to 200 kHz, which is coupled by an inductive rotary joint to the rotating part. The rotating part has control circuits and other components like a data acquisition system and a control computer in the case of CT (computed tomography) scanners which are all powered by the comparatively lower voltage. Other loads might be a drive inverter to control a cooling pump or fan. Furthermore the rotating side has at least one load which is relevant for safety. This may be an x-ray tube at a CT scanner. Unwanted enabling (activation) of the load may lead to personal injury or damage. Therefore enabling of the load must be controlled by a special control circuit.

When being fed by the first input circuit only, the AC power generator receives a comparatively lower DC voltage and therefore couples a comparatively lower voltage to the rotating part. In the case of being fed by the second input circuit, the AC power generator receives a comparatively higher DC voltage and therefore couples a comparatively higher voltage to the rotating part. This voltage at the rotating part may be any kind of AC or DC voltage. If the rotating part requires a DC voltage an additional rectifier may be provided between the secondary side of the inductive Rotary joint and the load or any component at the rotating part. A control unit located at the rotating part for controlling at least the load is connected to measure the voltage produced for the secondary side, and to distinguish between a comparatively lower voltage and a comparatively higher voltage. In a preferred embodiment the comparatively lower voltage is sufficient to supply at least a minimum of electronic components at the rotating part, preferably including the control unit. For the case of a comparatively higher voltage, the load is controlled, preferably activated accordingly. Preferably an x-ray tube is enabled within the load, when a comparatively higher voltage has been detected. The inventive safety function is switching a load at the rotating side from the primary side by changing the voltage level which is transferred over the rotary joint. This signaling only works if the power link including AC power generator, inductive rotary joint and further components necessary for transmission of power, like control circuits or rectifiers also work properly. Another advantage is that there is no additional signaling necessary from stationary to rotating side. The inventive concept is based on transferring different voltage levels. Therefore the means for generating such different voltage levels may be exchanged. Although using one and three phase rectifiers is the simplest way, any other combinations of rectifiers may be used. There may be any other circuit for generating different input voltage levels like transformers or power converters. Furthermore the voltage levels at the secondary side may be modified by controlling the switching frequency of the AC power generator. Such a modification of the voltage levels include switching on and off, generating comparatively higher and lower voltages and fine adjustment of the secondary voltage. Furthermore the switching frequency may be adjusted to at least one resonance frequency of the inductive rotary joint. The frequency may further be adjusted e.g. according to changes in temperature to compensate for temperature dependencies in parts of the inductive rotary joint like capacitors.

Switching or enabling the load may be done by a logic control signal (on/off) issued by the control circuit. Preferably the power supplied to the load is switched by a power switch between the secondary side of the inductive rotary joint and the load. This switch is controlled by the control circuit. There may be at least one power converter between the secondary side of the inductive rotary joint and the load or parts thereof. This may be a buck converter. Such a power converter may be enabled by the control circuit.

In a preferred embodiment the second input circuit has means for receiving an enable signal by which the power transfer by or through the second input circuit can be enabled or disabled. Such an enable signal may be received from a primary side control unit. It may also be received from a manual switch. Furthermore the enable signal may trigger a switch like a semiconductor switch or a mechanical switch within the second input circuit or it may trigger a main power switch. For the case the second input circuit has a power converter, this may be enabled or disabled by the enable signal.

In another preferred embodiment there is only an AC power generator coupled to an inductive rotary joint having a primary winding at the stationary part and a secondary winding at the rotating part for transferring the AC signal from the AC power generator coupled into the primary winding to the secondary winding. Furthermore there is a load at the rotating part connected to the secondary winding of the inductive rotary joint. The AC power generator together with the inductive rotary joint is enabled to produce a comparatively lower DC voltage at the secondary side or a comparatively higher DC voltage to the secondary side. Producing these different voltage levels may be triggered by receiving a comparatively lower DC voltage or a comparatively higher DC voltage at the input of the AC power generator or by receiving a control signal by a control unit located at the primary side. Furthermore there is a control unit located at the secondary side which is connected to measure the voltage produced for the secondary side, to distinguish between a comparatively lower DC voltage and a comparatively higher DC voltage and to enable the load when a comparatively higher DC voltage is measured at the secondary side. This embodiment may be combined with all other modifications and embodiments disclosed herein. Furthermore there may be more than two different voltage levels generated by the AC power generator coupled to the inductive rotary joint. The control unit located at the secondary side may then be enabled to distinguish between these different levels and to enable different loads or parts thereof.

Another embodiment is based on controlling the AC power generator for delivering different voltage levels to the rotating side. Accordingly the AC power generator may receive a constant input voltage and may receive control signals to deliver different voltage levels to the rotating side. This may also be used in conjunction with variable input voltages. If the difference between the comparatively lower voltage and the comparatively higher voltage at the input of the AC power generator is not sufficient, this may be amplified by appropriate control of the power generator so that the comparatively lower voltage may be further decreased and/or the comparatively higher voltage may be further increased at the rotating side.

Preferably the AC power generator and the inductive rotary joint are designed to have an approximately linear transmission characteristic of the voltage at the load compared to the DC voltage at the input of the AC power generator. At least this characteristic should be considered when dimensioning the control unit on the secondary side.

Preferably the second input circuit is connected to an external line, which preferably is a three phase line, by a main power switch. Most preferably the second input circuit is a three phase rectifier which is connected to an external three phase line by a main power switch. Only when this main power switch is on and/or the second input circuit is enabled, three phase power is fed to the second input circuit generating a comparatively higher voltage of the input of the AC power generator. This results in a comparatively higher voltage at the load and in and activation of the load by the control unit on the secondary side. Accordingly the circuit provided is comparable to an extension of the main power switch to the rotating part. Due to the comparatively high power levels transferred even by the comparatively low voltage at the load, this system is comparatively immune against electromagnetic interference (EMI). It can be made immune against a first component fault by monitoring the voltage at the load or any fault conditions of components at the secondary state. Due to physical limitations there can only be comparatively higher voltage at the load if the three-phase input is activated and the main power switch has been switched on.

In a preferred embodiment at least one of the first input circuit which may be a one phase rectifier and the second input circuit which may be a three phase rectifier including a power converter which may be a power factor control circuit. It preferably isolates the circuits from the power line(s).

In a further embodiment the first input circuit and/or the second input circuit may have a battery.

In another embodiment the primary side control unit is connected to measure a DC voltage at the input of the AC power generator to distinguish between a comparatively lower DC voltage and a comparatively higher DC voltage and to generate a corresponding output signal. The same function has a connection to the output of the second input circuit to check whether a valid voltage is delivered by that second input circuit. Another functionally equivalent embodiment would be to connect the control circuit to measure at least one current from at least one of the input circuits to distinguish whether the second input circuit is delivering power or not. The control circuit may also have an input for an auxiliary load disable signal. When such a load disable signal is received, the output signal (power, duty factor, frequency) are adjusted, so that the control unit receives a lower voltage and signals a comparatively lower DC voltage resulting in disabling the load.

In a further embodiment the primary side control unit is enabled to check whether the DC voltage values at the input of the AC power generator are within pre-determined limits for a comparatively lower DC voltage and a comparatively higher DC voltage and to generate a corresponding output signal.

In another embodiment the primary side control unit is enabled to switch off the AC power generator if the DC voltage values at the input of the AC power generator are outside of the pre-determined limits for a comparatively lower DC voltage and a comparatively higher DC voltage.

In a further embodiment control unit is connected to verify whether the voltage produced for the secondary side is within a predetermined window before enabling the load. It may further issue an error signal.

In another embodiment control unit is connected to check functional parameters of devices at the rotating side before enabling the load. Such functional parameters may be supply voltage, supply current and operating temperature. The control unit may further issue an error signal.

In another embodiment control unit is connected to check functional parameters of the load, which may be load current or load temperature. If the load is an x-ray tube, the radiation may also be checked.

In another embodiment the secondary side of the inductive rotary joint has a plurality of outputs being connected to separate parts of the load. The plurality of outputs may include different voltage or power outputs like a low voltage output for control circuitry, a low voltage and high current output for a computer system and a high voltage output for the x-ray tube. These different outputs may be connected to power converters and may have different control circuits to deliver controlled voltages to the separate parts of the load. There are also means for enabling parts of the load or for enabling individual or groups of outputs of the inductive rotary joint or power converters. Preferably the control unit is connected to one or more of these outputs of the secondary side and/or at least one of the control circuits connected thereto to check the parameters and to verify whether the output voltages delivered and/or the currents delivered are within a specified range. Furthermore specific parts of the load are enabled upon this verification. In an example there is a 24V/1 A supply for the basic control circuit, a 12V/20 A supply for a computer and an X-ray HV supply. Only when the supply voltage of the basic control circuit is within a specified range, the power converter supplying the computer is enabled. Only if the computer's supply voltage is a specified range and the computer is running, the X-ray HV supply is enabled.

BRIEF DESCRIPTION OF THE DRAWINGS

In the following, the invention will be described by way of example, without limitation of the general inventive concept, on examples of embodiment and with reference to the drawings.

DETAILED DESCRIPTION OF THE PREFERRED EMBODIMENTS

Figure 1:
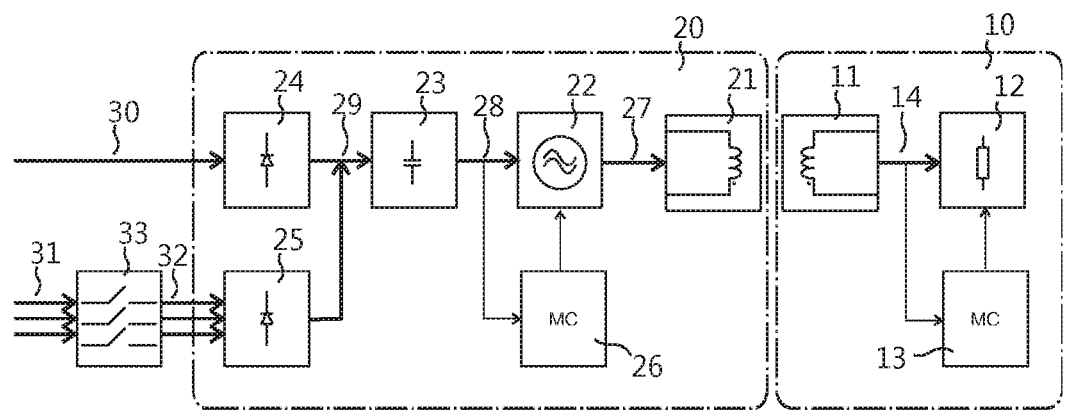
FIG. 1 shows a device in accordance with the invention.

In FIG. 1 a preferred embodiment is shown. On the stationary part 20 an inductive rotary joint system has a first input circuit as a one phase rectifier 24 for receiving a one phase AC input 30, generating a comparatively lower DC voltage at the output of the one phase rectifier. Furthermore a second input circuit as a three phase rectifier 25 is provided for receiving a three phase input 32 connected by a main power switch 33 to an external three phase AC line 31, generating a comparatively higher DC voltage and output of the three-phase rectifier. This main power switch 33 may also be a part of the second input circuit. The tree phase input is preferably connected by a main power switch 33, preferably an x-ray main switch to an external three phase AC power line. The DC voltage (29) generated by the rectifiers is filtered by a filtering circuit 23. An AC power generator 22 generates an AC signal 27 from the DC voltage, which is coupled by an inductive rotary joint 21, 11 to a load 12 at the rotating side 10. When being connected to the one phase AC input 30 only, the AC power generator receives a comparatively lower DC voltage and therefore couples a comparatively lower voltage to the load 12. In the case of being connected to the three phase AC input 32, the AC power generator receives a comparatively higher DC voltage and therefore couples a comparatively higher voltage to the load 12. A control unit 13 located at the rotating parts 10 for controlling at least the load is connected to measure the voltage produced for the secondary side 14, and to distinguish between a comparatively lower voltage and a comparatively higher voltage there. For the case of a comparatively higher voltage 14, the load is controlled accordingly. This means that parts of the load may be switched on and off according to the voltage level. Preferably an x-ray tube is enabled within the load. An optional primary side control unit 26 is connected to measure the DC voltage 28 at the output of the rectifiers and controls the AC power generator 22 accordingly.

Figure 2:
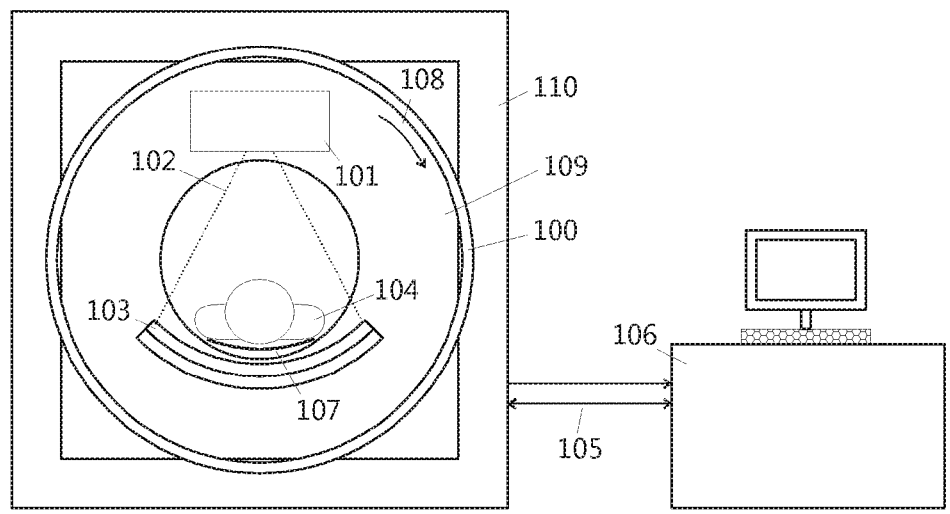
FIG. 2 shows an illustration of principle of a computer tomograph.

FIG. 2 shows schematically the construction of a computer tomograph having an inductive rotating transmission device. The stationary part of the rotating transmission device is suspended within a massive frame 110. The rotating part of the gantry 109 is rotatable mounted with respect to this and rotates along the rotation direction 108. Here is located an X-ray tube 101 for generating an X-ray beam 102 that radiates through a patient 104 lying on a table 107 and is intercepted by a detector 103 and converted to electrical signals. For transmitting the electrical energy from an energy supply unit, a rotary joint system 100 for inductively coupling electrical power is provided. Here the primary side is disposed on the stationary part and the secondary side on the rotating part. The data obtained by the detector 103 are transmitted to an evaluation unit 106. A control bus 105 serves for this, with which also the gantry itself can be controlled from the evaluation unit. While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

It will be appreciated to those skilled in the art having the benefit of this disclosure that this invention is believed to provide inductive rotary joints systems, such as collimators, used for transmission of electrical signals. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS 10 rotating part of CT scanner
11 secondary side of inductive rotary joint
12 load on the secondary side
13 control unit on the secondary side
14 voltage at secondary side
20 stationary part of CT scanner
21 primary side of inductive Rotary joint
22 AC power generator
23 filtering circuit
24 first input circuit
25 second input circuit
26 primary side control unit
27 AC signal from AC power generator 28 DC voltage at the input of the AC power generator
29 DC voltage generated by rectifiers
30 one phase AC input
31 external three phase AC line
32 three phase power path from main power switch to 3 phase rectifier
33 main power switch
100 inductive rotary joint system
101 X-ray tube
102 X-ray beam
103 detector
104 patient
105 control bus
106 evaluation unit
107 table
108 rotation direction
109 rotating part of gantry
110 stationary frame of gantry

What is claimed is:

1. A rotary joint system having stationary and rotating parts for inductively coupling electrical power between the stationary part and the rotating part, the rotary joint system comprising:
   first and second input circuits for converting an AC power line voltage into a DC voltage,
   an AC power generator adapted to received the DC voltage and to generate an AC power from the DC voltage,
   an inductive rotary joint having a primary side, a secondary side, the stationary part and the rotating part, a primary winding at the stationary part and a secondary winding at the rotating part, the AC power generator being operably coupled into the primary winding, said inductive rotary joint configured to transfer the AC power from the AC power generator to the secondary winding,
   a load at the rotating part operably connected to the secondary winding of the inductive rotary joint,
   a control unit located at a primary side coupled with and configured to control at least the AC power generator, and
   a control unit located at the secondary side coupled with and configured to control at least the load, and
   wherein:
   the first input circuit is configured to generate a first DC voltage that is lower than a nominal DC voltage and the second input circuit is configured to generate a second DC voltage that is higher than the nominal DC voltage, outputs of the first and second input circuits being operably connected to deliver power to the AC power generator,
   the AC power generator and the inductive rotary joint aggregately produce (i) a third DC voltage at the secondary side when the AC power generator receives the first DC voltage and (ii) a fourth DC voltage at the secondary side when the AC power generator receives the second DC voltage, the third DC voltage being lower than the nominal DC voltage and the fourth DC voltage being higher than the nominal DC voltage, and
   the control unit located at the secondary side is adapted to measure the voltage produced for the secondary side, to distinguish between the third DC voltage and the fourth DC voltage, and to enable the load when the fourth DC voltage is measured at the secondary side.

2. A rotary joint system according to claim 1, wherein the first input circuit includes a one-phase rectifier with corresponding filtering means, said one-phase rectifier configured to receive a one-phase input.

3. A rotary joint system according to claim 2, wherein the second input circuit includes is a three-phase rectifier with corresponding filtering means, said three-phase rectifier configured to receive a three-phase input.

4. A rotary joint system according to claim 3, wherein at least one of the one-phase rectifier and the three-phase rectifier includes a power factor control circuit.

5. A rotary joint system according to claim 1, wherein the second input circuit includes at least one of means for enabling power and a main power switch.

6. A rotary joint system according to claim 1, wherein the outputs the first and second input circuits are connected in parallel.

7. A rotary joint system having stationary and rotating parts for inductively coupling electrical power between the stationary part to the rotating part, the rotary joint system comprising:
   an AC power generator configured to receive a DC voltage and generate an AC output from the DC voltage,
   an inductive rotary joint having a primary side, a secondary side, a primary winding at the stationary part and a secondary winding at the rotating part, the primary winding being operably coupled to the AC power generator, the inductive rotary joint configured to transfer the AC output received from the AC power generator to the secondary winding,
   a load, at the rotating part, operably connected to the secondary winding of the inductive rotary joint, and
   a control unit located at the secondary side and configured to enable at least the load,
   wherein:
   the AC power generator in cooperation with the inductive rotary joint are enabled to produce at least one of a first DC voltage at the secondary side and a second DC voltage at the secondary side, the first voltage being lower than a nominal DC voltage and the second voltage being higher than the nominal DC voltage, and
   the control unit located at the secondary side is configured to measure voltage produced at the secondary side, to distinguish said voltage between said first DC voltage and said second DC voltage, and to enable the load when said second DC voltage is measured at the secondary side; and
   further comprising a control unit at the primary side that is configured to control the AC power generator,
   wherein the AC power generator together with the inductive rotary joint are configured to produce one of (i) the first DC voltage at the secondary side, when receiving a third DC voltage that is lower than the nominal DC voltage, (ii) the second DC voltage at the secondary side, when receiving a fourth DC voltage that is higher than the nominal DC voltage, and (iii) the second DC voltage at the secondary side, when receiving a control signal from the control unit at the primary side.

8. A rotary joint system according to claim 7, wherein said control unit at the primary side is configured to verify whether a DC voltage at the input of the AC power generator is within a range defined by said third and fourth DC voltages and to generate an output, to the AC power generator, when such a condition is satisfied.

9. A rotary joint system according to claim 7, wherein said control unit at the primary side is configured to switch off the AC power generator when a DC voltage at the input of the AC power generator is outside of a range defined by said third and fourth DC voltages.

10. A rotary joint system according to claim 7, wherein the load includes an x-ray tube.

11. A rotary joint system according to claim 7, wherein the secondary side of the inductive rotary joint has a plurality of outputs respectively connected to different parts of the load.

12. A rotary joint system according to claim 11, further comprising power converters operably attached to outputs from the plurality of outputs, wherein the control unit located at the secondary side is adapted to measure values of at least one of voltage and current associated with at least one of said outputs and power converters, and to enable remaining outputs and power converters when measured values are within a specified range.

13. A rotary joint system according to claim 7, wherein the control unit located at the secondary side is configured to perform at least one of
   a) a verification of whether a voltage produced for the secondary side is within a predetermined range and
   b) a verification of functional parameters of devices at the rotating part, before enabling the load.

14. A rotary joint system according to claim 7, wherein the control unit located at the secondary side is configured to verify functional parameters of the load.

15. A rotary joint system according to claim 7, wherein the AC power generator is configured to control the switching frequency of the AC power generator to modify a voltage level at the secondary side.

* * * * *